(12) United States Patent
Boldingh et al.

(10) Patent No.: US 8,242,321 B2
(45) Date of Patent: Aug. 14, 2012

(54) PROCESSES FOR TRANSALKYLATING AROMATIC HYDROCARBONS

(75) Inventors: Edwin P. Boldingh, Arlington Heights, IL (US); Antoine Negiz, Wilmette, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/894,204

(22) Filed: Sep. 30, 2010

(65) Prior Publication Data

US 2012/0083635 A1    Apr. 5, 2012

(51) Int. Cl.
    *C07C 6/12* (2006.01)
(52) U.S. Cl. ..................................................... 585/475
(58) Field of Classification Search .................. 585/475
    See application file for complete search history.

(56) References Cited

U.S. PATENT DOCUMENTS

| | | | |
|---|---|---|---|
| 3,527,825 A * | 9/1970 | Pollitzer | .................. 585/474 |
| 5,177,285 A | 1/1993 | Van Opdorp | |
| 6,740,788 B1 | 5/2004 | Maher et al. | |
| 6,855,854 B1 | 2/2005 | James | |
| 6,867,340 B2 * | 3/2005 | Oh et al. | .................. 585/475 |
| 7,220,885 B2 | 5/2007 | Boldingh et al. | |
| 7,605,295 B1 * | 10/2009 | Lafyatis et al. | .................. 585/475 |
| 7,626,064 B1 | 12/2009 | Boldingh et al. | |
| 7,687,423 B2 | 3/2010 | Moscoso et al. | |

OTHER PUBLICATIONS

U.S. Appl. No. 12/894,209, filed Sep. 30, 2010, Boldingh.
U.S. Appl. No. 12/882,400, filed Sep. 15, 2010, Boldingh.
Jeanneret, Chapter 2.7: UOP Tatoray Process, Handbook of Petroleum Refining Processes, 2nd Ed., 1997, McGraw-Hill, USA, ISBN 0-07-041796-2, pp. 2.55-2.62.

* cited by examiner

*Primary Examiner* — Thuan Dinh Dang
(74) *Attorney, Agent, or Firm* — Mark R Willis

(57) ABSTRACT

A process for transalkylating aromatic hydrocarbon compounds, the process comprising introducing an aromatic hydrocarbon feed stream and a water source to a transalkylation zone. The feed stream contacts a catalyst in the transalkylation zone in the presence of water, and produces a reaction product stream comprising benzene and xylene. The invention includes methods to control the transalkylation process.

10 Claims, No Drawings

PROCESSES FOR TRANSALKYLATING AROMATIC HYDROCARBONS

FIELD OF THE INVENTION

The present invention generally relates to improved processes for transalkylating aromatic hydrocarbon compounds. More particularly the invention relates to aromatic transalkylation processes producing xylenes and benzene.

DESCRIPTION OF RELATED ART

Xylene isomers ("xylenes") and benzene are produced in large volumes from petroleum by the reforming of naphtha. However, neither the xylenes nor benzene are produced in sufficient volume to meet demand. Consequently, other hydrocarbons are necessarily converted to increase the yield of the xylenes and benzene via processes such as transalkylation, disproportionation, isomerization, and dealkylation. For example, toluene commonly is dealkylated to produce benzene. Alternatively, or additionally, toluene can be disproportionated to yield benzene and $C_8$ aromatics from which the individual xylene isomers are recovered.

More recently, development has been directed at selectively transalkylating heavier aromatics, such as $C_9+$ aromatics, with toluene and/or benzene to increase the yield of xylenes and benzene from aromatics complexes. In this regard, a variety of catalysts have been developed for these processes. For example, a wide range of zeolites, including mordenite, have been disclosed as effective transalkylation catalysts. Shaped catalysts, multiple zeolites, metal modifiers, and treatments such as steam calcination have been described as increasing the effectiveness of the catalysts.

Known catalysts are effective for producing xylenes and benzene. Specifically, catalysts having a sufficient metal function are suitable to convert heavier aromatics, such as $C_9+$ aromatics to xylenes and benzene and provide improved catalyst stability in a transalkylation process. However, in transalkylation processes employing such catalysts, aromatic rings may become saturated or even cleaved resulting in naphthene and acyclic paraffin (non-aromatics) co-production, which can result in a loss of valuable aromatics. Also, because some of the non-aromatics have similar boiling points to benzene (benzene co-boilers), they are not readily removed to achieve a benzene product having a desired purity for commercial applications. Although the benzene co-boilers can be fractionated or extracted with a solvent, such processes are expensive and typically require additional equipment.

Accordingly, it is desirable to provide a transalkylation process that produces a high purity benzene product. In another aspect, it is desirable to provide a transalkylation process to that produces less benzene co-boilers. Other desirable features and characteristics of the present invention will become apparent from the subsequent detailed description of the invention and the appended claims.

SUMMARY OF THE INVENTION

It has been discovered that introducing water into a transalkylation zone reduces the production of benzene co-boilers and/or improves the purity of the benzene fraction of the transalkylation reaction product stream. In another aspect, the invention enables control of the purity of a benzene product stream and/or control of the amount of benzene co-boilers relative to benzene in the reaction product stream or fraction thereof.

In an embodiment, the invention is a process for transalkylating aromatic hydrocarbon compounds comprising introducing a water source and the aromatic hydrocarbon compounds to the transalkylation zone. The feed stream is contacted with a catalyst in the transalkylation zone under transalkylation conditions including the presence of water. A reaction product stream comprising benzene and xylene is produced. In an exemplary embodiment, the catalyst comprises an aluminosilicate zeolite component having an MOR framework type, an MFI molecular sieve component having a $Si/Al_2$ molar ratio of less than 80, an inorganic oxide binder, and a metal component comprising a metal selected from the group consisting of rhenium, nickel, cobalt, molybdenum, tungsten, tin, germanium, lead, indium, platinum, palladium, and combinations thereof.

In another embodiment, the invention is a method for controlling an aromatic transalkylation process comprising introducing aromatic hydrocarbon compounds and a water source to a transalkylation zone. Contacting the feed stream with a catalyst in the transalkylation zone under transalkylation conditions including the presence of water. Producing a benzene product stream, determining a purity of the benzene product stream, and controlling the introduction of the water source in response to the purity of the benzene product stream.

DETAILED DESCRIPTION

The aromatic hydrocarbons to be transalkylated by processes of the invention include alkylaromatic hydrocarbons of the general formula $C_6H_{(6-n)}R_n$, where n is an integer from 0 to 5 and R is $CH_3$, $C_2H_5$, $C_3H_7$, or $C_4H_9$, in any combination. Non-limiting examples include: benzene, toluene, ethylbenzene, ethyltoluenes, propylbenzenes, tetramethylbenzenes, ethyl-dimethylbenzenes, diethylbenzenes, methylethylbenzenes, methylpropylbenzenes, ethylpropylbenzenes, triethylbenzenes, trimethylbenzenes, di-isopropylbenzenes, and mixtures thereof. The feed stream may comprise lower levels of ortho-xylene, meta-xylene, and para-xylene that are desired products of the process.

As used herein, the term "transalkylation" encompasses transalkylation between and among alkyl aromatics, between benzene and alkyl aromatics, and it includes dealkylation and disproportionation, e.g., of toluene to benzene and xylene. The aromatic hydrocarbons also may comprise naphthalene and other $C_{10}$ and $C_{11}$ aromatics. Herein, hydrocarbon molecules may be abbreviated $C_1$, $C_2$, $C_3$, . . . $C_n$, where "n" represents the number of carbon atoms in the hydrocarbon molecule. Such abbreviations followed by a "+" is used to denote that number of carbon atoms or more per molecule, and a "−" is used to denote that number of carbon atoms or less per molecule.

Polycyclic aromatics having from 2 to 4 rings are permitted in the feed stream of the present invention. Non-limiting examples include: indanes, naphthalenes, tetralins, decalins, biphenyls, diphenyls and fluorenes. Indane is meant to define a nine carbon atom aromatic species with one ring of six carbon atoms and one ring of five carbon atoms wherein two carbon atoms are shared. Naphthalene is meant to define a ten carbon atom aromatic species with two rings of six carbon atoms wherein two carbon atoms are shared.

The aromatic hydrocarbons to be transalkylated may be introduced to the transalkylation zone in one or more feed streams. As used herein, the term "zone" can refer to one or more equipment items and/or one or more sub-zones. Equipment items may include, for example, one or more vessels, heaters, separators, exchangers, conduits, pumps, compressors, and controllers. Additionally, an equipment item can further include one or more zones or sub-zones. In embodiments having multiple feed streams, the feed streams may be introduced separately to the transalkylation zone, or two or more of the feed streams may be combined in any manner prior to passing them into the transalkylation zone.

The feed streams may be derived from one or more sources including, without limitation, catalytic reforming, pyrolysis of naphtha, distillates or other hydrocarbons to yield light olefins and heavier aromatics-rich byproducts, and catalytic or thermal cracking of heavy oils to yield products in the gasoline range. Products from pyrolysis or other cracking operations generally will be hydrotreated according to processes well known in the industry before being charged to the transalkylation zone in order to remove sulfur, olefins and other compounds which would affect product quality. Light cycle oil also may be beneficially hydrocracked to yield lighter components which can be reformed catalytically to yield the aromatics-rich feed stream. If the feed stream is catalytic reformate, the reformer preferably is operated at high severity for high aromatics yield with a low concentration of non-aromatics in the product. The reformate may also be subjected to olefin saturation to remove potential product contaminants and materials that could polymerize to heavy non-convertibles in a transalkylation process. Such processing steps are described in U.S. Pat. No. 6,740,788 B1, which is incorporated herein by reference thereto.

A feed stream can include a substantially pure alkylaromatic hydrocarbon of from about 6 to about 15 carbon atoms, a mixture of such alkylaromatic hydrocarbons, or a hydrocarbon fraction rich in said alkylaromatics. A feed stream also may contain lesser concentrations of non-aromatics such as pentanes, hexanes, heptanes and heavier paraffins along with paraffins along with methylcyclopentane, cyclohexane and heavier naphthenes; pentanes and lighter paraffins generally will have been removed before processing. The combined transalkylation feed preferably contains no more than about 10 wt % non-aromatics; and olefins preferably are restricted to a Bromine Index of no more than about 1000, and preferably no more than about 500.

In an embodiment, at least two feed streams are introduced to the transalkylation zone, a light feed stream and a heavy feed stream. The light aromatic feed stream may comprise at least one of benzene and toluene. Preferred components of the heavy aromatic feed are $C_9+$ aromatics, thereby effecting transalkylation of toluene and $C_9+$ aromatics to yield additional xylenes. Benzene may also be transalkylated to yield additional toluene. Indane may be present in the heavy aromatics feed stream although it is not a desirable component to effect high yields of xylenes in the transalkylation zone effluent. $C_{10}+$ aromatics also may be present, preferably in an amount of 30% or less of the heavy aromatic feed. The heavy aromatic feed stream preferably comprises at least about 90 mass % aromatics, and may be derived from the same or different known refinery and petrochemical processes as the benzene/toluene feed stream and/or may be recycled from the separation of the transalkylation effluent.

The aromatic feed to a transalkylation reaction zone is usually first heated by indirect heat exchange against the reaction product stream and then is heated to reaction temperature by exchange with a warmer stream, steam or a furnace. The feed is preferably transalkylated in the vapor phase and in the presence of hydrogen. In an embodiment a hydrogen stream is introduced to the transalkylation zone. The hydrogen stream may comprise other compounds, e.g. $C_1$ to $C_4$ hydrocarbons, in addition to hydrogen. Hydrogen and hydrocarbons may be recycled in the process as described below. If present, free hydrogen is associated with the feedstock and recycled hydrocarbons, if any, in an amount from about 0.1 moles per mole of aromatics up to 10 moles per mole of aromatics. This ratio of hydrogen to aromatics is also referred to as hydrogen to hydrocarbon ratio.

The feed then is passed through one or more reactors containing the transalkylation catalyst to produce a reaction product stream comprising unconverted feed and product hydrocarbons including xylenes and benzene. This reaction product stream is normally cooled by indirect heat exchange against the aromatic feed stream entering the transalkylation zone and may be further cooled through the use of air or cooling water. The reaction product stream may be separated e.g. in a vapor-liquid separator to produce a vapor phase hydrogen stream and a liquid phase reaction product stream. The vapor phase hydrogen stream includes hydrogen and light hydrocarbons which may be recycled and combined with the feed as described above. The liquid phase reaction product stream may be passed into a stripping column in which substantially all C5 and lighter hydrocarbons present are concentrated into an overhead stream and removed from the process. As used herein, the term "substantially all" means an amount generally of at least 90%, preferably at least 95%, and optimally at least 99%, by weight, of a compound or class of compounds in a stream. The stripping column also produces a net stripper bottoms stream, which is referred to herein as the transalkylation zone effluent.

The transalkylation zone effluent may be further separated in a distillation zone comprising at least one distillation column to produce a benzene product stream. Various flow schemes and combinations of distillation columns to separate transalkylation zone effluent via fractional distillation are well known in the art. In addition to the benzene product stream, the distillation zone may produce a toluene product stream, and a $C_8+$ product stream. See, e.g., U.S. Pat. No. 7,605,295. It is also known that the transalkylation zone stripper column may be designed and operated to produce a benzene product stream. See, e.g., U.S. Pat. No. 6,740,788. Thus, the reaction product stream contains a benzene fraction that may be separated by fractional distillation to produce a benzene product stream.

In another embodiment, the transalkylation effluent is separated into a light recycle stream, a mixed $C_8$ aromatics product, and a heavy aromatic product stream in a distillation zone. The mixed $C_8$ aromatic product may be sent for recovery of para-xylene and/or other isomers. The light recycle stream may be diverted to other uses such as benzene and toluene recovery, but may be recycled, in part, to the transalkylation zone. The heavy recycle stream contains substantially all of the $C_9$ and heavier aromatics and may be partially or totally recycled to the transalkylation reaction zone.

The invention also requires introducing a water source into the transalkylation zone. The water source may be introduced as a separate stream into the transalkylation zone, and/or the water source may be combined with an aromatic feed stream and/or a hydrogen containing stream. The water source may comprise water or other compounds containing oxygen that will decompose to produce water in the transalkylation zone. Typical examples of water sources, include without limitation, any alcohol, aldehyde, epoxide, ketone, phenol, and ether. Preferably, the water source has a molecular weight or boiling point within the range of molecular weights or boiling points of the hydrocarbons in the feed or hydrogen containing streams. The water source may comprise methanol, ethanol, propanol ethyl ether, methyl tert-butyl ether, isopropyl ether, and tertiary butyl alcohol.

In an embodiment, the water source is introduced to the transalkylation zone in an amount to provide more than 100 ppm-wt of water based upon the mass of the feed stream. The amount of water provided by a water source is the amount of water that would result from the water source converting to water in the process. The amount of water provided by a water source is readily determined by one of ordinary skill in the art. The mass of a water source and the mass of the feed are used to determine the amount of water source, e.g. ppm-wt based on the mass of the feed. This value is multiplied by a factor equal to the weight of water that would be produced per weight of water source converted to obtain the amount of water provided by the water source based upon the mass of the feed. The factor is 0.56 for methanol ($CH_3OH$) and 0.58 for ethylene glycol ($C_2H_4(OH)_2$).

In another embodiment, the water source is introduced to the transalkylation zone in an amount to provide at least about 125 ppm-wt of water, and may provide at least about 150 ppm-wt, and optionally at least about 300 ppm-wt of water based upon the mass of the feed stream. In a further embodiment, the water source is introduced to the transalkylation zone in an amount to provide from more than 100 ppm-wt of water to about 1000 ppm-wt of water based upon the mass of the feed stream. In another embodiment the water source is introduced to the transalkylation zone in an amount to provide from at least about 125 ppm-wt to about 1000 ppm-wt, and may provide from at least about 150 ppm-wt to about 800 ppm-wt of water based upon the mass of the feed stream.

The aromatic feed stream introduced into the transalkylation zone contacts the catalyst at transalkylation conditions to produce the reaction product stream which comprises comprising unconverted feed, xylenes, and benzene. The transalkylation conditions include the presence of water. In an embodiment, the water is in the vapor phase. Without wishing to be bound by any particular theory, it is believed that the water modifies or attenuates the metal function of the catalyst to reduce the amount of benzene co-boilers that would otherwise be produced, thus increasing the purity of the benzene fraction of the reaction product stream. As used herein the term "benzene co-boilers" means non-aromatic hydrocarbon compounds having 6 or 7 carbon atoms per molecule. Benzene co-boilers that are particularly difficult to separate from benzene by fractional distillation include cyclohexane; methylcyclopentane; 2,3-dimethylpentane; 3-methylhexane; and dimethylcyclopentane.

The water source may be introduced into the transalkylation zone continuously at a constant rate, or the rate of water source addition may vary during the process cycle, e.g. as the feed quality varies, as the catalyst deactivates, and as processing objectives such as the degree of conversion change. A process cycle runs from the initial introduction of feed until the process is discontinued to regenerate or replace the catalyst. A process cycle may be measured in a variety of ways including: time on stream (i.e. time feed is being introduced); the quantity of feed that has been introduced, e.g. mass or volume of feed processed; and the quantity of feed (mass or volume) per quantity of catalyst (mass or volume), e.g. barrels (feed) per pound (catalyst) (BPP), cubic meters of feed (e.g. at standard or normal conditions) per mass or volume of catalyst. A process cycle may be temporarily suspended or halted by discontinuing feed introduction. If suspended for an extended period of time, the unit may be held in a stand-by mode. However, the length of the process cycle will continue to accrue once feed introduction resumes, provided the catalyst has not been regenerated or replaced. In another embodiment, the water source is added intermittently during the process cycle.

In a further embodiment, the water source is introduced when the feed is initially introduced to the transalkylation zone. During the initial portion of the process cycle, the catalyst usually exhibits the highest activity; therefore, the operating temperatures are usually at a minimum. These conditions typically result in higher amounts of benzene co-boilers and lower benzene purity. The catalyst ages and deactivates as the process cycle continues and to maintain the desired level of conversion the reactor temperature may be increased. The amount of water source addition may be decreased as the process cycle continues and the reaction temperature increases. Without wishing to be bound by any particular theory, it is believed that benzene co-boilers are cracked more efficiently by the acid sites on the catalyst, especially the MFI zeolite, as the temperature increases. At some point in the process cycle, water source introduction may no longer be required, e.g. to obtain the desired benzene product purity.

In an embodiment, the water source is introduced intermittently or continuously during the initial one-third of the process cycle. In another embodiment, the water source is introduced intermittently or continuously during the initial one-fifth (20%) of the process cycle; and the water source may be introduced intermittently or continuously during the initial one-tenth (10%) of the process cycle. To determine a portion or fraction of a process cycle herein, the process cycle and the fraction thereof are determined on the basis of mass of feed per mass of catalyst, e.g. metric ton of feed per metric ton of catalyst.

In an embodiment, the purity of the benzene product may be controlled by adjusting the rate of water source introduced in response to a determination of the benzene product purity. Benzene purity may be determined by analysis of the benzene product stream and/or from a determination of the amount of benzene co-boilers relative to the amount of benzene. For example, the amount of benzene co-boilers relative to the amount of benzene may be determined in any of the reaction product stream, the transalkylation zone effluent stream, and the benzene product stream. The determination of benzene purity and the relative amount of the benzene co-boilers may be performed by manually obtaining samples and analyzing them off-line or by automatic on-line analysis. Changing the rate of water source introduction in response to the determination may be done manually or through the use of a control system as is known in the art. The manual and automatic modes of these steps may be combined in any manner. For example, an on-line analyzer may determine the amount of benzene co-boilers relative to the amount of benzene in the reaction product stream and send a signal to a process controller. The process controller may in turn send a signal to a control valve that regulates the rate of water source addition. Algorithms, such as to convert the relative amount of co-boilers to a purity of the benzene product steam may include terms to account for the fractional distillation efficiency and/or time lags in the process, and may be applied in or by any of the analyzer, controller, and control valve to generate or interpret the signals. Such techniques are well known in the art of process control.

Contacting the feed and water with the catalyst can be effected in any conventional or otherwise convenient manner and may occur as a batch or continuous type of operation. In an embodiment, the catalyst is disposed in one or more fixed beds in a reaction zone of a vertical reactor with the aromatic feed and water charged through the bed in an upflow or downflow manner. Transalkylation conditions may include a temperature in a range of from about 200° C. to about 540° C., preferably between about 200° C. to about 480° C.; a pressure in a range of from about 100 kPa to about 6 MPa absolute; and a weight hourly space velocity (WHSV, i.e., weight of aromatic feed introduced per weight of catalyst per hour) in a range of from about 0.1 to about 20 hr$^{-1}$.

In an embodiment, the invention includes a transalkylation catalyst comprising: an aluminosilicate zeolite having an MOR framework type, an MFI molecular sieve having a Si/Al$_2$ molar ratio of less than 80, a metal component comprising a metal selected from the group consisting of rhenium, nickel, cobalt, molybdenum, tungsten, tin, germanium, lead, indium, platinum, palladium, and combinations thereof, and an inorganic oxide binder.

Aluminosilicate zeolite having an MOR framework is described in ATLAS OF ZEOLITE FRAMEWORK TYPES, 6th Revised Edition, C. H. Baerlocher, L. B. McCusker, and D. H. Olson, editors, Elsevier (2007), pp. 218-219. The MOR framework comprises four- and five-membered rings of SiO$_4$ and AlO$_4$ tetrahedra to form a crystal lattice comprising 12-ring channels running parallel along a crystal axis to give a tubular configuration. In an embodiment, the aluminosilicate zeolite having an MOR framework comprises mordenite. Where mordenite is a component of the catalyst, the mordenite preferably has a Si/Al$_2$ molar ratio of less than about 40. The Si/Al$_2$ molar ratio of mordenite in an embodiment is less than about 25, and in another embodiment the mordenite Si/Al$_2$ molar ratio is between about 15 and about 25. Mordenite may be synthesized with a Si/Al$_2$ molar ratio of between about 10 and about 20. Mordenite is preferably at least partially in the hydrogen form and/or may be dealuminated by a variety of techniques, e.g. steaming, and acid extraction of aluminum to increase the Si/Al$_2$ ratio of the mordenite.

In another embodiment, the aluminosilicate zeolite having an MOR framework comprises UZM-14. UZM-14 is described in U.S. Pat. No. 7,687,423, which is incorporated herein by reference in its entirety. UZM-14 comprises globular aggregates of crystallites having a MOR framework type comprising 12-ring channels, and one or more of the following distinctive characteristics: a mesopore volume of at least about 0.10 cc/gram, preferably at least about 0.13 cc/gram, more preferably at least about 0.2 cc/gram; a mean crystallite length parallel to the direction of the 12-ring channels of about 60 nm or less, preferably about 50 nm or less; a Si/Al$_2$ mole ratio of between about 8 and about 50, and preferably is no more than about 30; and at least about 1×10$^{19}$ 12-ring channel openings per gram of UZM-14 material.

In an embodiment, UZM-14 comprises globular aggregates of crystallites having a MOR framework type comprising 12-ring channels, a silica-alumina mole ratio of from about 8 to no more than about 30, a mesopore volume of at least about 0.10 cc/gram, and a mean crystallite length parallel to the direction of the 12-ring channels of about 60 nm or less.

UZM-14 has an empirical composition in the as-synthesized form on an anhydrous basis expressed by the empirical formula:

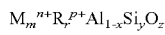

where M is at least one exchangeable cation and is selected from the group consisting of alkali and alkaline earth metals including but not limited to lithium, sodium, potassium, rubidium, cesium, calcium, strontium, barium and mixtures thereof. R is at least one organic cation selected from the group consisting of protonated amines, protonated diamines, quaternary ammonium ions, diquaternary ammonium ions, protonated alkanolamines, and quaternized alkanolammonium ions. Relating the components, "m" is the mole ratio of M to Al and varies from about 0.05 to about 0.95; "r" is the mole ratio of R to Al and has a value of about 0.05 to about 0.95; "n" is the weighted average valence of M and has a value of about 1 to about 2; "p" is the weighted average valence of R and has a value of about 1 to about 2; "y" is the mole ratio of Si to Al and varies from about 3 to about 50; and "z" is the mole ratio of 0 to Al and has a value determined by the equation: z=(m·n+r·p+3+4y)/2.

The catalyst also includes an MFI molecular sieve having a Si/Al$_2$ molar ratio of less than 80. Zeolites having an MFI type framework are described in ATLAS OF ZEOLITE FRAMEWORK TYPES, 6th Revised Edition, C. H. Baerlocher, L. B. McCusker, and D. H. Olson, editors, Elsevier (2007). MFI type zeolites have a 3-dimensional 10-ring channel system: [100] 10-MR 5.1×5.5 Å and [010] 10-MR 5.3×5.6 Å. In an embodiment, MFI molecular sieves used in the catalysts of this invention have a Si/Al$_2$ molar ratio of less than about 40, preferably less than about 25, for example, between about 15 to about 25. An example of a suitable MFI molecular sieve for inclusion in the catalyst includes, but is not limited to, ZSM-5, which is disclosed in U.S. Pat. No. 3,702,886, incorporated herein, by reference thereto. Suitable MFI molecular sieves are also available, for example, from Zeolyst International of Conschocken, Pa. and Tosoh Corporation of Tokyo, Japan.

In an embodiment, the MFI molecular sieve has a "Total Acidity" of at least about 0.15, preferably at least about 0.25, and more preferably at least about 0.4, for example, 0.4 to 0.8. Total Acidity is determined by Ammonia Temperature Programmed Desorption (Ammonia TPD). The Total Acidity of the MFI molecular sieve may be that of the MFI to be used in making the catalyst of the invention or may be achieved during the preparation of the catalyst. Typically, the MFI molecular sieve is at least partially in the hydrogen form in the finished catalyst. The Ammonia TPD process involves first heating a sample (about 250 milligrams) of molecular sieve at a rate of about 5° C. per minute to a temperature of about 550° C. in the presence of a 20 volume percent oxygen in helium atmosphere (flow rate of about 100 milliliters per minute). After a hold of about one hour, helium is used to flush the system (about 15 minutes) and the sample is cooled to about 150° C. The sample is then saturated with pulses of ammonia in helium at about 40 milliliters per minute. The total amount of ammonia used is greatly in excess of the amount required to saturate all the acid sites on the sample. The sample is purged with helium (about 40 milliliters per minute) for about 8 hours to remove physically adsorbed ammonia. With the helium purge continuing, the temperature is increased at a rate of about 10° C. per minute to a final temperature of 600° C. The amount of ammonia desorbed is monitored using a calibrated thermal conductivity detector. The total amount of ammonia is found by integration. Dividing the total amount of ammonia by the dry weight of the sample yields the Total Acidity. As used herein, values of Total Acidity are given in units of millimoles of ammonia per gram of dry sample.

The inorganic oxide binder of the catalyst comprises such materials as alumina, silica, zirconia, titania, thoria, boria, magnesia, chromia, stannic oxide, and the like as well as combinations and composites thereof, for example silica-alumina, alumina-zirconia, alumina-titania, aluminum phosphate, and the like. Alumina is a preferred refractory inorganic oxide binder. As is well known in the art, a precursor of the desired refractory inorganic oxide may be used to form, bind, and/or otherwise prepare the catalyst. Such binder precursors or sources may be converted into a refractory inorganic oxide binder, e.g. by calcination. The alumina may be any of the various aluminum oxides, hydroxides, and gels, including boehmite, pseudo-boehmite, gibbsite, bayerite, and the like, especially transition and gamma aluminas. Suitable aluminas are commercially available, e.g. under the trade names CATAPAL B and VERSAL 250.

The metal component of the catalyst comprises a metal selected from the group consisting of rhenium, nickel, cobalt, molybdenum, tungsten, tin, germanium, lead, indium, platinum, palladium, and combinations thereof. In an embodiment, metal component comprises a metal selected from the group consisting of rhenium, molybdenum, tin, germanium, indium, platinum, palladium, and combinations thereof. In an embodiment the metal content of the catalyst ranges from about 0.01 wt % to about 10.0 wt % as the metal based upon the total weight of the catalyst.

The metal component may be incorporated into the catalyst in any suitable manner such as comulling, coprecipitation or cogellation with the carrier material, ion exchange, or impregnation. The metal component may exist within the final catalyst as a compound such as an oxide, sulfide, halide, or oxyhalide, in chemical combination with one or more of the other ingredients of the composite, or as an elemental metal. One method of preparing the catalyst involves the use of a water-soluble or solvent-soluble, decomposable compound of the metal to impregnate the molecular sieve-containing support. Alternatively, a metal compound may be added at the time of compositing the molecular sieve component and binder.

The weight ratio of the MFI molecular sieve component to the aluminosilicate zeolite having the MOR framework may range from about 1:10 to 5:1, preferably from about 1:10 to 2:1. In an embodiment, the aluminosilicate zeolite component having the MOR framework comprises from about 20 wt % to about 80 wt % of the catalyst, the MFI molecular sieve component comprises from about 10 wt % to about 70 wt % of the catalyst, and the inorganic oxide binder comprises between about 1 wt % and about 40 wt % of the catalyst.

The catalyst may optionally include an additional molecular sieve component preferably selected from one or more of MEL, EUO, FER, MFS, MTT, MTW, MWW, MAZ, TON and FAU (IUPAC Commission on Zeolite Nomenclature) and UZM-8 (see U.S. Pat. No. 6,756,030 which is herein incorporated by reference in its entirety). The catalyst may optionally include a fluoride component in an amount ranging from about 0.1 wt % to about 5.0 wt % of fluoride based upon the total weight of the catalyst. The fluoride component may be incorporated into the catalyst by any known technique, e.g. impregnation.

The techniques used to prepare the catalyst are well known to those of ordinary skill in the art. The catalyst can be formed by combining the aluminosilicate zeolite component having the MOR framework, the MFI molecular sieve component, and the inorganic oxide binder and/or a precursor thereof in any conventional or otherwise convenient manner to form spheres, pills, pellets, granules, extrudates, or other suitable particle shapes. For example, finely divided aluminosilicate zeolite having the MOR framework and MFI molecular sieve particles, and metal salt particles can be dispersed in an alumina sol, and the mixture in turn dispersed as droplets in a hot oil bath whereby gelation occurs with the formation of spheroidal gel particles. A preferred method comprises mixing a finely divided form of the selected aluminosilicate zeolite having the MOR framework and MFI molecular sieve particles, a binder and/or precursor thereof, with a metal salt and, optionally, a lubricant; and compressing the mixture into pills or pellets. Alternatively, and still more preferably, the aluminosilicate zeolite having the MOR framework, MFI molecular sieve particles, binder and/or precursor thereof, and metal salt are combined and admixed with a peptizing agent in a mixer-muller, a dilute nitric acid being one example of the suitable peptizing agent. The resulting dough can be pressured through a die or orifice of predetermined size to form extrudate particles which can be dried and calcined and utilized as such. A multitude of different extrudate shapes are possible, including, but not limited to, cylinders, cloverleaf, dumbbell and symmetrical and asymmetrical polylobes, with a trilobe form being favored. The extrudates also may be formed into spheres by means of a spinning disc or drum. The variously formed particles are then usually dried and/or calcined.

If the metal component is not included in the above forming steps, or if an additional metal component is to be included, the formed particles produced above can be impregnated with a soluble, decomposable compound containing the metal component to form a composite. For example, when the metal component comprises molybdenum, typical compounds which may be employed include ammonium heptamolybdate, alkali metal molybdates (also peroxo-, di-, tri-, tetra-, hepta-, octa-, or tetradecamolybdate), molybdic acid, phosphomolybdic acid, Mo—P heteropolyanion compounds, acetyl acetonates, Mo(0) metal, Mo oxides, Mo peroxo complexes, and mixtures thereof. The composite is preferably calcined in an air atmosphere at a temperature of from about 425° C. to about 750° C., preferably at a temperature of from about 475° C. to about 600° C., over a period of from about 0.5 to about 10 hours. Typically, the formed particles are also calcined at similar conditions prior to the impregnation step. The catalyst preparation may include various optional steps such as drying and steaming which are well known in the art.

EXAMPLE 1

A catalyst was prepared by blending of UZM-14, MFI zeolite, and Catapal B to obtain a 50% UZM-14, 25% MFI zeolite, and 25% Catapal B mixture on a volatile free (VF) weight basis. The mixture also included a solution of ammonium heptamolybdate to obtain 0.5 wt % molybdenum (VF) in the final catalyst, and a solution of diluted nitric acid as the peptizing agent to form a dough. The dough was extruded as a cylinder and the catalyst was calcined at 500° C. for 2 hours in dry air. The UZM-14 zeolite used in this example was prepared according to Example 1 of U.S. Pat. No. 7,687,423. Prior to incorporation in the catalyst, the UZM-14 was ion exchanged with an ammonium sulfate solution to reduce the sodium content of the zeolite to less than 0.05 wt % sodium. The ion exchanged UZM-14 zeolite had the following properties: a $SiO_2/Al_2O_3$ molar ratio of 15.9, a BET surface area of 448 $m^2/g$, a micropore volume of 0.21 cc/gram, and a mesopore volume of 0.31 cc/gram. The MFI zeolite was CBV 2314, a ZSM-5 material with $SiO_2/Al_2O_3$ of 23, obtained from Zeolyst International. Catapal B was purchased from Vista Chemical Company. The finished catalyst had a BET surface area of 375 $m^2/g$, a total pore volume of 0.43 cc/g and a piece density of 1.232 g/cc.

EXAMPLE 2

The catalyst in this example was prepared in the same way as described in Example 1, except the final catalyst contained 3.0 wt % molybdenum (VF) and a prepared MFI component had a molar $SiO_2/Al_2O_3$ ratio of 38, a BET surface area of 351 $m^2/g$, a Langmuir surface area of 517 $m^2/g$, a micropore volume of 0.18 cc/gram and a mesopore volume of 0.21 cc/gram. The ion exchanged UZM-14 zeolite used in this example had the following properties: a molar $SiO_2/Al_2O_3$ ratio of 15.9, a BET surface area of 450 $m^2/g$, a micropore volume of 0.21 cc/gram and a mesopore volume of 0.29 cc/gram. The catalyst had a BET surface area of 355 m²/g and a total pore volume of 0.37 cc/g. The piece density was 1.246 g/cc.

EXAMPLE 3

The catalyst in this example was prepared in the same way and from the same materials as described in Example 1, except the final catalyst contained 5.0 wt % molybdenum (VF) and the extrudates were trilobes rather that cylinders. The catalyst had a BET surface area of 353 m²/g and a total pore volume of 0.40 cc/g. The piece density was 1.107 g/cc.

EXAMPLE 4

A catalyst was prepared by blending of mordenite, MFI zeolite, and Catapal B to obtain a 50% mordenite, 25% MFI zeolite, and 25% Catapal B mixture on a volatile free (VF) weight basis. The mixture also included a solution of ammonium perrhenate to obtain a catalyst with 0.15 wt % rhenium (VF) in the final catalyst, and a solution of diluted nitric acid as the peptizing agent to form a dough. The dough was extruded as a cylinder and the catalyst was calcined at 635° C. for 30 minutes in air with 15 mole % steam. The mordenite zeolite used in this example was CBV 21A, purchased from Zeolyst International having a molar $SiO_2/Al_2O_3$ ratio of 20.7, a BET surface area of 401 m²/g, a Langmuir surface area of 584 m²/g, a micropore volume of 0.20 cc/gram and a mesopore volume of 0.08 cc/gram. The MFI component was the same material as used in Example 2. The Catapal B was the same material as used in the other examples. The finished catalyst had a BET surface area of 345 m²/g, a total pore volume of 0.39 cc/g and a piece density of 1.229 g/cc.

EXAMPLE 5

The catalysts of Examples 1-4 were tested in an aromatics transalkylation test. Prior to testing, the catalysts were sulfided in-situ as is well known in the art to convert the metals (Mo and Re) and/or their oxides at least partially, to the metal sulfide. An objective of catalyst sulfiding is to add a fixed amount of sulfur to the catalyst. This was accomplished by passing excess dimethyl disulfide (DMDS), equivalent to 150 ppm-wt as sulfur, in the feed over the catalyst at a temperature of 280° C., a pressure of 1,724 kPa(g), a weight hourly space velocity of 4 and a hydrogen to hydrocarbon ratio of 6 for 26 hours. Catalyst sulfiding was continued at a temperature of 360° C. for 12 hours, followed by 2 hours at 350° C. This procedure provides a sulfided catalyst with a relatively fixed sulfur content such that longer sulfiding with excess DMDS will not increase the sulfur content of the catalyst any further. After the sulfiding procedure was complete, feed without a sulfur source was continued to the catalyst for 10 hours as transalkylation conditions were lined out for testing. The following were common to all stages of the test. A pressure of 1,724 kPa(g), a weight hourly space velocity of 4 and a hydrogen to hydrocarbon ratio of 6. Product samples were obtained hourly throughout all stages of the test and were analyzed to determine the benzene purity calculated as benzene/(benzene+$C_6$ and $C_7$ non-aromatics) on a weight percent basis.

Stage 1 was conducted at 350° C. to establish a base line "dry" performance during the first 10 hours of testing. To ensure the feed had essentially zero water, the feed for all stages of the test was dried first through 3A/13X molecular sieve driers followed by high surface area sodium driers. No water source was added in Stage 1. Tertiary-butyl alcohol (TBA) was then introduced to the dry feed to provide 150 ppm-wt of water based on the mass of the feed stream to begin Stage 2. After 15 hours at these conditions, the TBA was increased to provide 300 ppm-wt of water based on the mass of the feed stream to begin Stage 3. After 7 hours at Stage 3 conditions, the TBA was removed from the feed and water was purged from the system for about 15 hours when dry steady state conditions at 350° C. were attained in Stage 4. The reaction temperature was then increased to 365° C. and baseline dry data was obtained for 10 hours at the higher temperature in Stage 5. TBA was then introduced to the dry feed for 15 hours in Stage 6 to provide 150 ppm-wt of water based on the mass of the feed stream. Finally, the TBA was removed from the feed stream to re-establish dry conditions in Stage 7. The feed had nominally the composition in weight percent given in Table 1. The results for the steady state operation of each stage are reported below in Table 2.

TABLE 1

| Toluene | 75 |
| Propylbenzene | 2.0 |
| Methylethylbenzene | 10 |
| Trimethylbenzene | 9.7 |
| Indane | 0.8 |
| Methylpropylbenzene | 1.0 |
| Diethylbenzene | 0.4 |
| Dimethylethylbenzene | 1.0 |
| $C_{11}$+ aromatics | 0.1 |

TABLE 2

| Stage | Temperature, ° C. | Water level in feed, ppm-wt | Catalyst of Example # | Benzene Purity (wt %) |
|---|---|---|---|---|
| 1 | 350 | dry | 1 | 99.75 |
| 1 | 350 | dry | 2 | 99.05 |
| 1 | 350 | dry | 3 | 99.10 |
| 1 | 350 | dry | 4 | 98.80 |
| 2 | 350 | 150 | 1 | 99.75 |
| 2 | 350 | 150 | 2 | 99.30 |
| 2 | 350 | 150 | 3 | 99.35 |
| 2 | 350 | 150 | 4 | 98.80 |
| 3 | 350 | 300 | 1 | 99.75 |
| 3 | 350 | 300 | 2 | 99.35 |
| 3 | 350 | 300 | 3 | 99.35 |
| 3 | 350 | 300 | 4 | 98.80 |
| 4 | 350 | dry | 1 | 99.75 |
| 4 | 350 | dry | 2 | 98.80 |
| 4 | 350 | dry | 3 | 98.80 |
| 4 | 350 | dry | 4 | 98.70 |
| 5 | 365 | dry | 1 | 99.85 |
| 5 | 365 | dry | 2 | 99.20 |
| 5 | 365 | dry | 3 | 99.25 |
| 5 | 365 | dry | 4 | 99.25 |
| 6 | 365 | 150 | 1 | 99.85 |
| 6 | 365 | 150 | 2 | 99.50 |
| 6 | 365 | 150 | 3 | 99.55 |
| 6 | 365 | 150 | 4 | 99.25 |
| 7 | 365 | dry | 1 | 99.85 |
| 7 | 365 | dry | 2 | 99.20 |
| 7 | 365 | dry | 3 | 99.25 |
| 7 | 365 | dry | 4 | 99.20 |

There is no intention to be bound by any theory presented herein. As is well know to those skilled in the art, water can interact with zeolitic acid sites and attenuate the acidity. However, if that were the case here, the conversion/cracking of the non-aromatic benzene co-boilers should be impaired, resulting in lower benzene purity. In contrast, the data in Table 2 show little to no measurable effect of water on the benzene purity for the catalysts of examples 1 and 4. More surprisingly, for the catalysts of examples 2 and 3, water clearly increases the benzene purity. This suggests that the water interacts with the metal function instead of the acid function. However, it is believed an effect would be observed for examples 1 and 4 if the operating conditions were changed to produce a less pure benzene stream and/or the amount of rhenium in example 4 were increased.

The data in Table 2 shows the effect of water to be reversible. As discussed above, processes according to the invention may introduce a water source in the earlier portion of a process cycle to improve benzene purity, for example, when a catalyst is generally more active. As the catalyst ages, the operating temperature is usually increased to maintain a desired conversion level and the purity of the benzene product improves so that addition of a water source may be reduced or discontinued.

The invention claimed is:

1. A process for transalkylating aromatic hydrocarbon compounds, the process comprising:
   introducing a feed stream comprising the aromatic hydrocarbon compounds to a transalkylation zone;
   introducing a water source to the transalkylation zone, the water source being in an amount to provide more than 100 ppm-wt. of water based upon the mass of the feed stream;
   contacting the feed stream with a sulfided catalyst comprising an aluminosilicate zeolite component having an MOR framework type selected from the group consisting of UZM-14 and mordenite; an MFI molecular sieve component; an inorganic oxide binder comprising a material selected from the group consisting of alumina, silica, zirconia, titania, thoria, boria, magnesia, chromia, stannic oxide, and combinations thereof; and between about 3% and about 5% molybdenum in the transalkylation zone under transalkylation conditions including the presence of water;
   producing a reaction product stream comprising benzene and xylene;
   wherein the process has a process cycle and the water source is introduced during the initial one-tenth of the process cycle as determined by the mass of the feed introduced per mass of the catalyst;
   separating the reaction product stream to produce a benzene product stream; and
   wherein the water source is introduced intermittently and a purity of the benzene product stream is higher during a period of water source introduction relative to a period without water source introduction.

2. The process of claim 1 wherein water source is introduced to the transalkylation zone in an amount to provide at least about 125 ppm-wt. of water based upon the mass of the feed stream.

3. The process of claim 1 wherein the water source is introduced to the transalkylation zone in an amount to provide from more than 100 ppm-wt. of water to about 1000 ppm-wt. of water based upon the mass of the feed stream.

4. The process of claim 1 wherein water is present in the vapor phase.

5. The process of claim 1 wherein the water source is selected from the group consisting of alcohols, aldehydes, epoxides, ketones, phenols, ethers, and combinations thereof.

6. The process of claim 1 wherein the feed stream comprises at least one of a C9+ aromatic compound and toluene.

7. The process of claim 1 wherein the aluminosilicate zeolite comprises mordenite.

8. The process of claim 1 wherein the aluminosilicate zeolite comprises UZM-14.

9. The process of claim 1 wherein the MFI molecular sieve comprises ZSM-5.

10. The process of claim 1 wherein the inorganic oxide binder comprises alumina.

* * * * *